United States Patent [19]

Cornsweet et al.

[11] 4,019,813
[45] Apr. 26, 1977

[54] OPTICAL APPARATUS FOR OBTAINING MEASUREMENTS OF PORTIONS OF THE EYE

[75] Inventors: Tom N. Cornsweet; Richard A. Harrison, both of Houston, Tex.

[73] Assignee: Baylor College of Medicine, Houston, Tex.

[22] Filed: Jan. 19, 1976

[21] Appl. No.: 650,391

[52] U.S. Cl. .......................... 351/14; 178/DIG. 36; 351/6; 351/40
[51] Int. Cl.² ...................... A61B 3/10; A61B 3/14
[58] Field of Search ................. 351/6, 7, 9, 14, 39, 351/40; 178/DIG. 1, DIG. 36; 28/2 T

[56] References Cited
UNITED STATES PATENTS

| | | | |
|---|---|---|---|
| 3,536,384 | 10/1970 | Cocks | 351/6 |
| 3,639,041 | 2/1972 | Cornsweet | 351/6 X |
| 3,740,468 | 6/1973 | Gardner et al. | 178/DIG. 36 |
| 3,908,079 | 9/1975 | Worthley | 178/DIG. 36 |
| 3,909,519 | 9/1975 | Page, Jr. | 178/DIG. 36 |
| 3,980,870 | 9/1976 | Kawahara | 178/DIG. 36 |

OTHER PUBLICATIONS

George Cocks, "An Instrument for Measuring the Contour of the Cornea," Applied Optics, vol. 7, No. 1, pp. 151–154, Jan. 1968.

Primary Examiner—Paul A. Sacher
Attorney, Agent, or Firm—Fulbright & Jaworski

[57] ABSTRACT

An optical apparatus for obtaining one or more measurements of portions of an eye having means for providing a narrow beam of light through the eye, a lens system that collects light that is reflected from the eye and forms an image on the surface of a television camera tube and including means for determining when the narrow beam of light passes through the center of curvature of the cornea and when the instrument is correctly positioned for proper focus on the eye. Means are connected to the television camera for receiving and processing the video signals while the camera scans the image of the eye for measuring various portions of the eye such as the thickness of the cornea, the curvature of the leading edge of the cornea, the depth of the anterior chamber, the thickness of the lens, the transparency of the cornea, the transparency of the aqueous humor, and the transparency of the lens.

22 Claims, 11 Drawing Figures

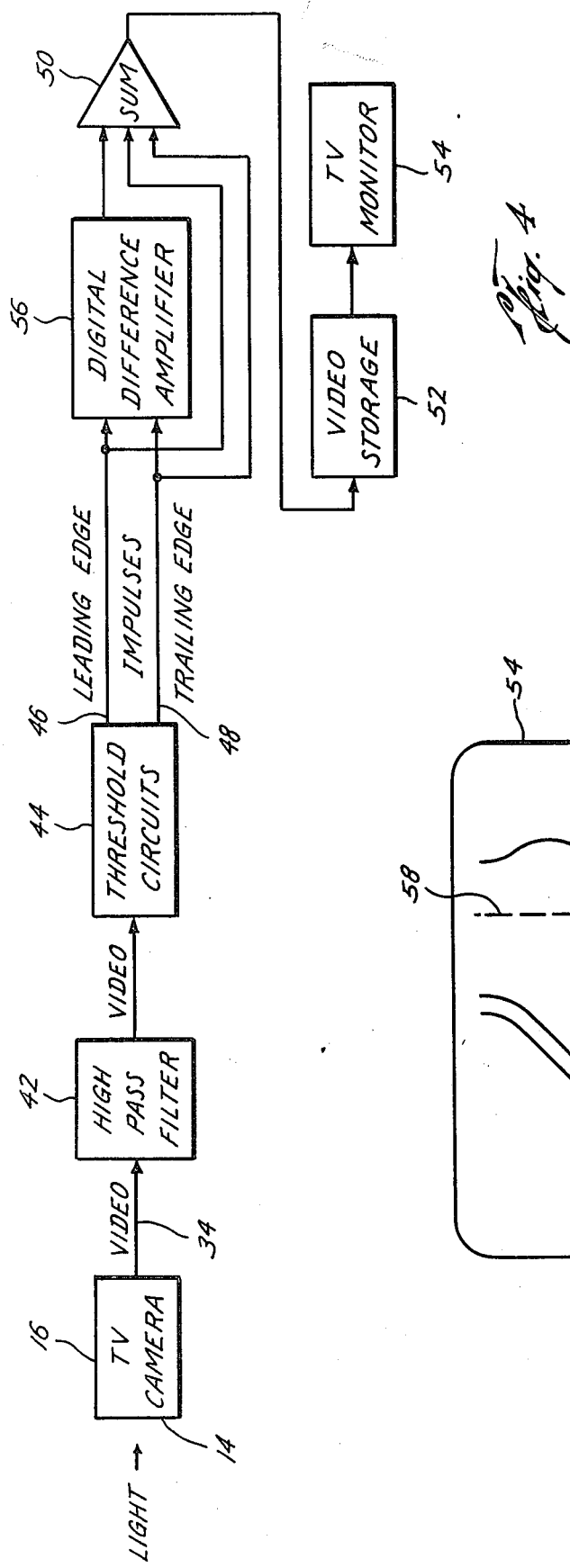

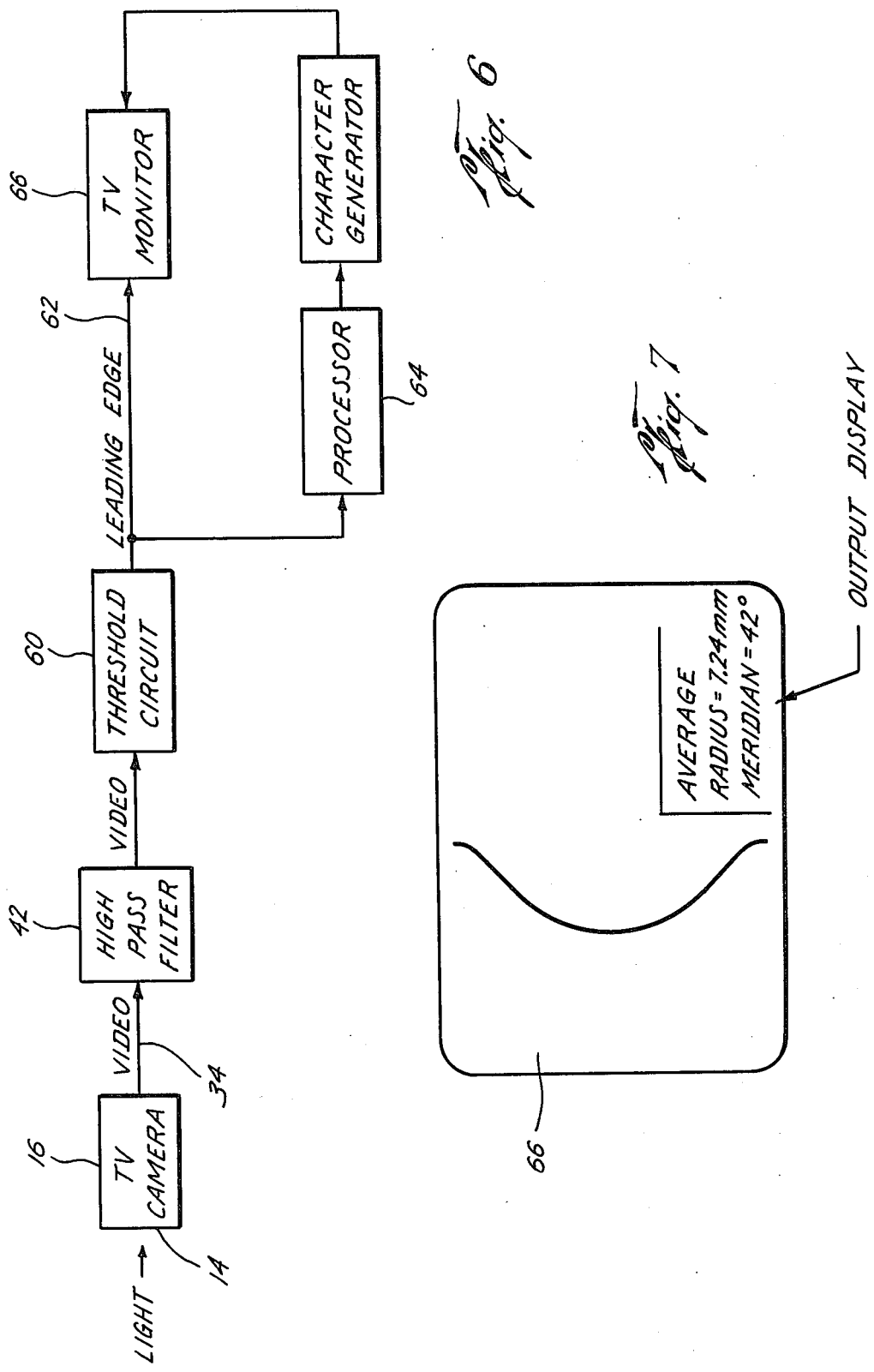

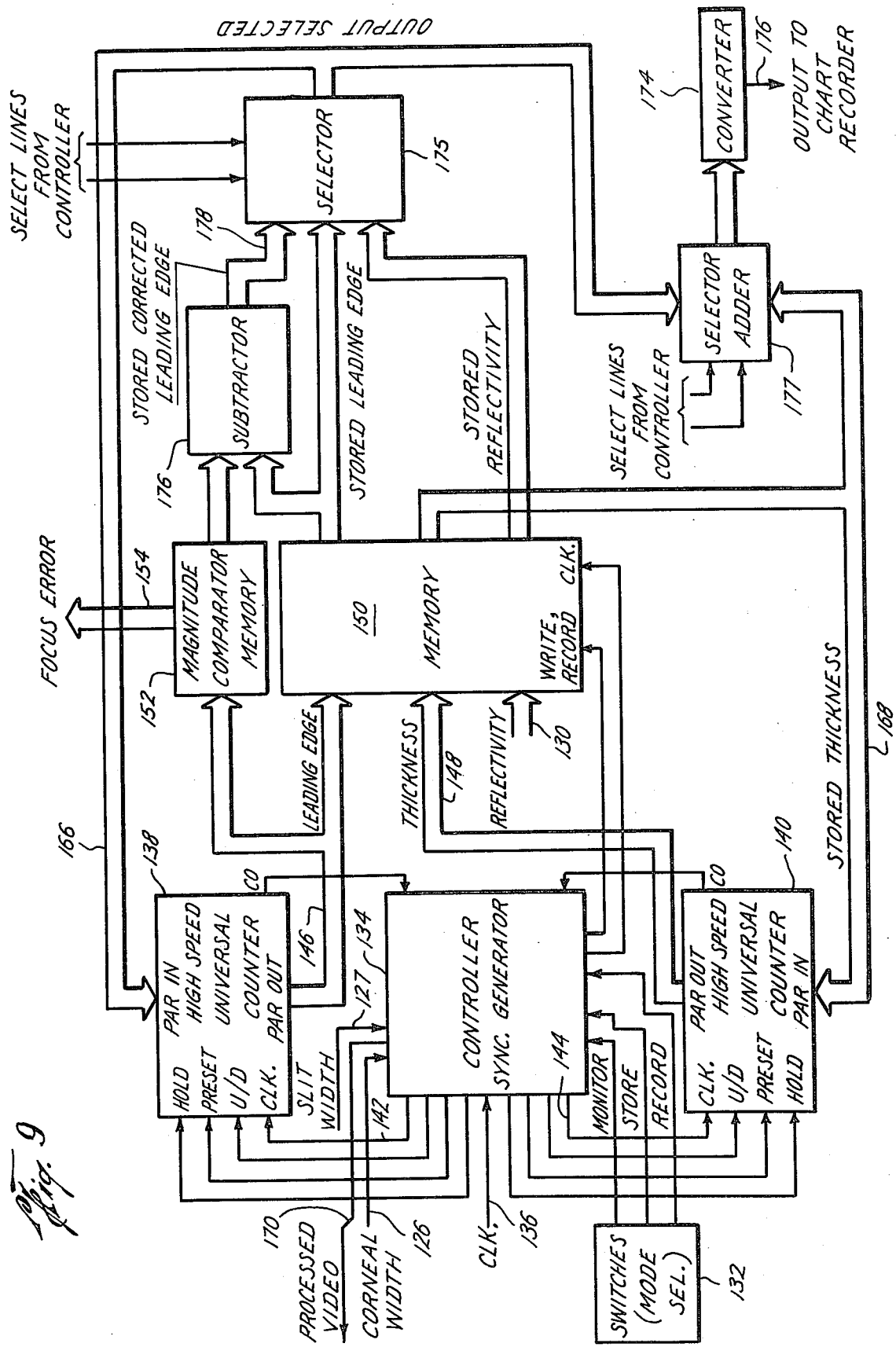

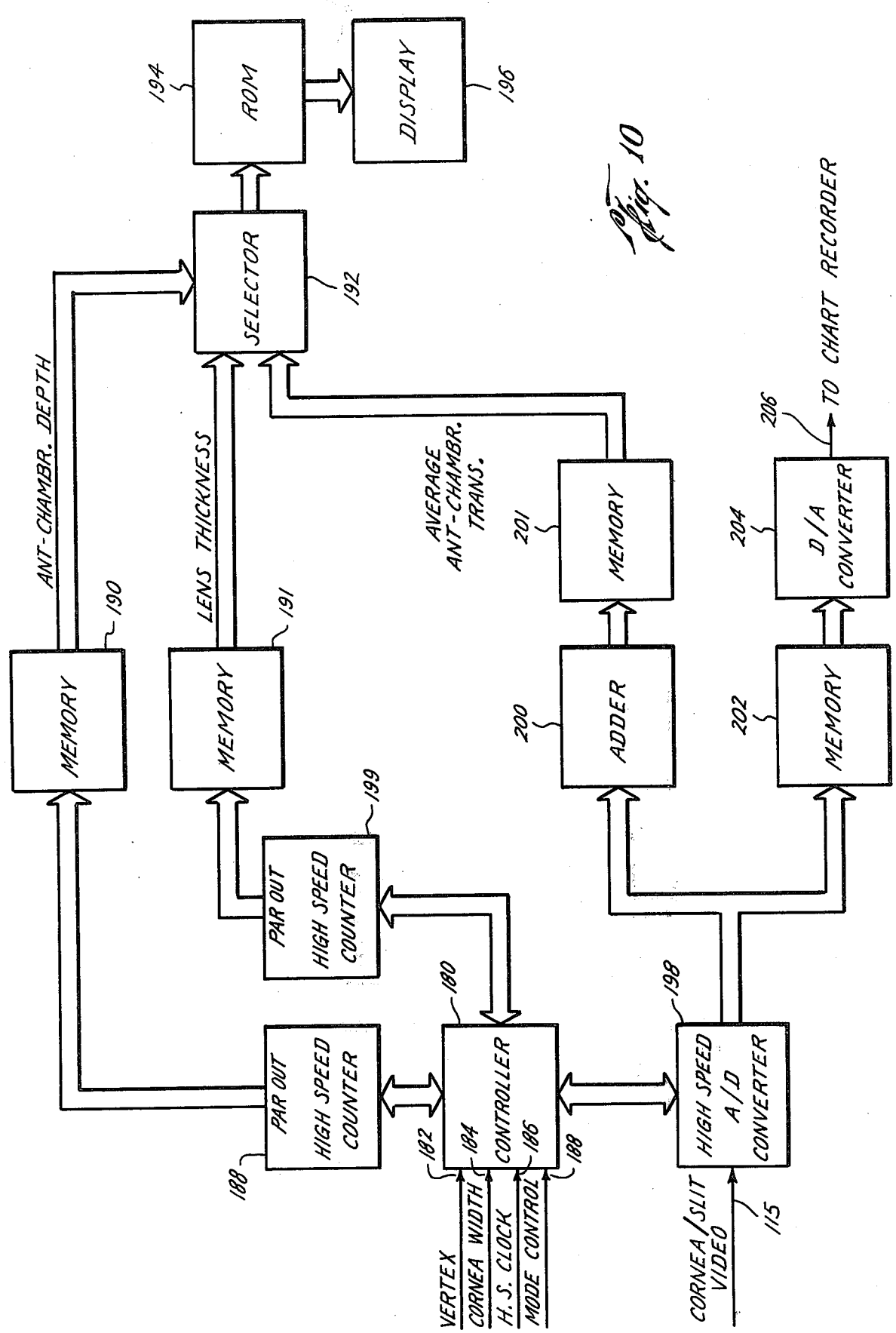

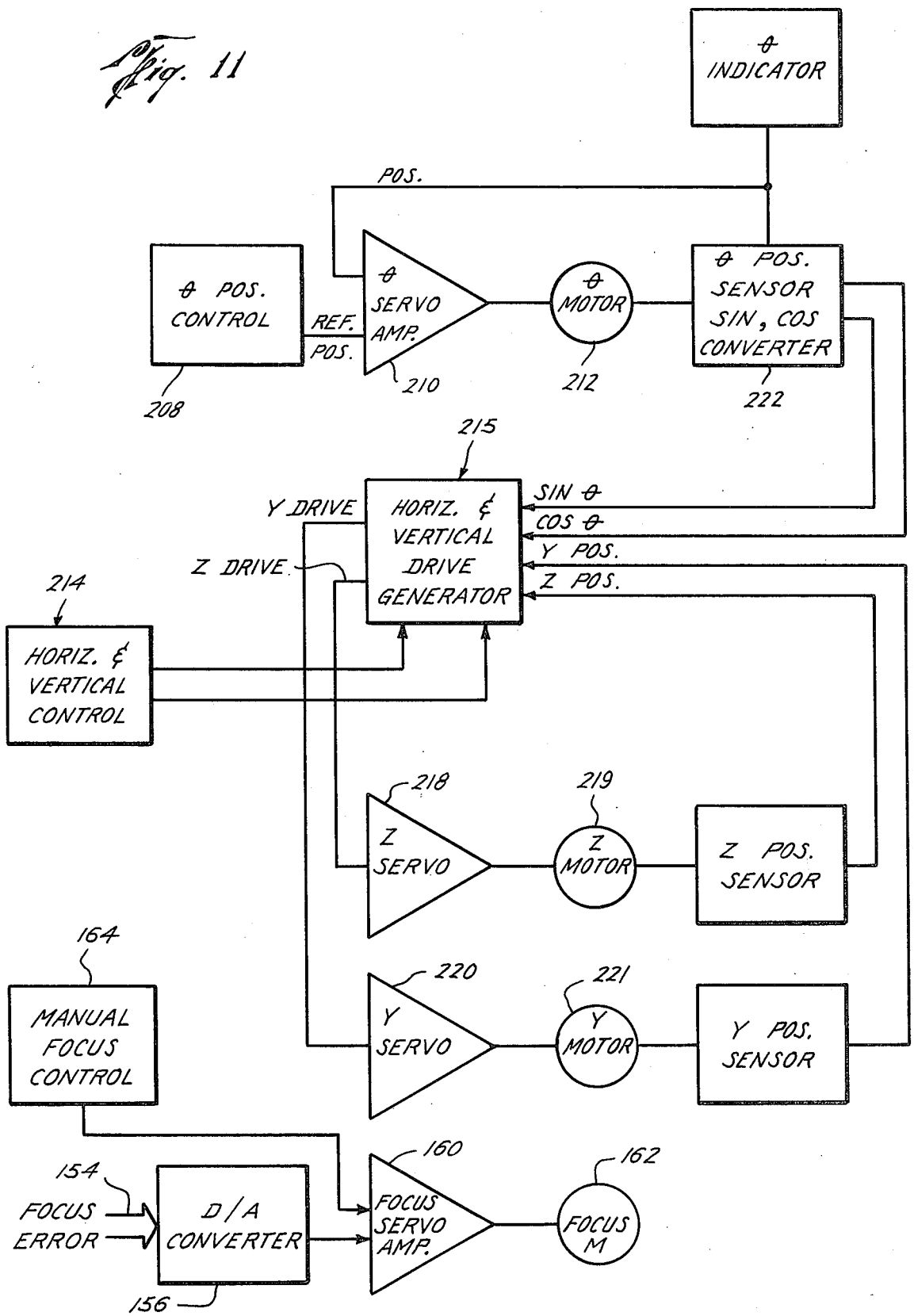

OPTICAL APPARATUS FOR OBTAINING MEASUREMENTS OF PORTIONS OF THE EYE

BACKGROUND OF THE INVENTION

It is often desirable to obtain accurate measurements of various portions of a patient's eye. At the present time, ophthalmologists use an instrument called a "slit lamp" to observe visually the thickness of the cornea, and some slit lamps are equipped with attachments that permit the photographing of what the ophthalmologist sees through the instrument. However, visual observations made with the slit lamp are not inherently quantitative, and to obtain accurate quantitative data from slit lamp photographs requires elaborate and laborious procedures to insure that the photographs are accurately measured and that the angular relationships between the various elements of the slit lamp are accurately recorded and compensated for. In addition to obtaining measurements of the thickness of the cornea, it is often desirable, particularly when a patient is being fitted with contact lenses, to know the curvature of the surface of the patient's cornea. In addition, other measurements of the eye, such as the depth of the anterior chamber, the thickness of the lens, and the transparency of the cornea, the anterior chamber and the lens are of great interest to ophthalmologists.

The present invention is directed to an electrooptical apparatus for obtaining one or more measurements of portions of an eye to provide accurate data which may be used in diagnosing eye problems, treating eye problems, and generally increasing the knowledge of eye pathology.

SUMMARY

The present invention is generally directed to an electro-optical apparatus for obtaining one or more measurements of the eye in which a light source, first lens means and one or more slits provide a narrow beam of light through the cornea of the eye. A second lens means is positioned in front of the eye but at an angle to the narrow beam of light for collecting light that is reflected from the eye and the image of the eye structure is projected onto a television camera. In order to obtain accurate data, the optical apparatus must be accurately related to the eye. In order to insure that the narrow beam of light has a known location with respect to various features of the eye, means are provided for measuring the relationship between the beam of light and the center of curvature of the cornea for properly adjusting the optical apparatus relative to the eye. In addition, the distance between the instrument and the eye must be controlled in order to insure proper focus of the image of the eye on the television tube and suitable means are provided for measuring this relationship.

A further object of the present invention is the provision of positioning the television camera to receive the image collected by the second lens means at an angle to the optical axis of the second lens means for improving the sensitivity of the system for measurements of thickness and curvature as well as increasing the depth of focus of the image of the eye.

Still a further object of the present invention is the provision of means connected to the television camera receiving the video signals of the camera for measuring the leading and trailing edges of various eye structures such as the cornea and the lens whereby the difference between the leading and trailing edge measurements provide a measurement of the thickness of the cornea, the depth of the anterior chamber, and the thickness of the lens. In addition, storage means are provided for storing the measured data.

Yet a still further object of the present invention is a provision of means connected to the television camera including a processor for receiving the data relative to the leading edge of the cornea for determining the shape of the leading edge of the cornea.

Still a further object of the present invention is the provision of means for rotating the optical apparatus about the optical axis of the first lens means for obtaining measurements along various meridians of the eye.

Yet still a further object of the present invention is the provision of means for maintaining the light output of the light source constant whereby changes in the voltage to and age of the light source does not adversely affect the measurements.

Still a further object of the present invention is the provision of means connected to the television camera for receiving the video signals and measuring the intensity of the signals to provide a measurement of the transparency of various portions of the eye such as the cornea, the anterior chamber, and the lens.

A still further object of the present invention is the provision of means for reflecting a portion of the narrow beam of light onto the television camera and comparing the intensity of the video signals corresponding to the transparency of the portion of the eye being measured with the intensity of the reflected beam of light on the camera along each horizontal line for reducing problems of changes in intensity and of noninformities of the illuminating beam.

Other and further objects, features and advantages will be apparent from the following description of a presently preferred embodiment, given for the purpose of disclosure and taken in conjunction with the accompanying drawings.

BRIEF DESCRIPTION OF THE DRAWINGS

FIG. 4 is an electrical block diagram illustrating a principle of operation used for measuring the thickness of the cornea, FIG. 5 is the output of the circuit shown in FIG. 4 as shown on the video storage device of FIG. 4, FIG. 6 is an electrical block diagram showing a principle of operation used for measuring the radius of curvature of the leading edge of the cornea, FIG. 7 is the output of the circuit of FIG. 6 shown on the video monitor of FIG. 6, FIG. 9 is a block diagram of the logic circuitry of the preferred embodiment of the present invention, FIG. 10 is a block diagram of an additional logic circuit for further measurements of the present invention, and FIG. 11 is a block diagram of the apparatus positioning servos of the present invention.

DESCRIPTION OF THE PREFERRED EMBODIMENT

Figure 1:
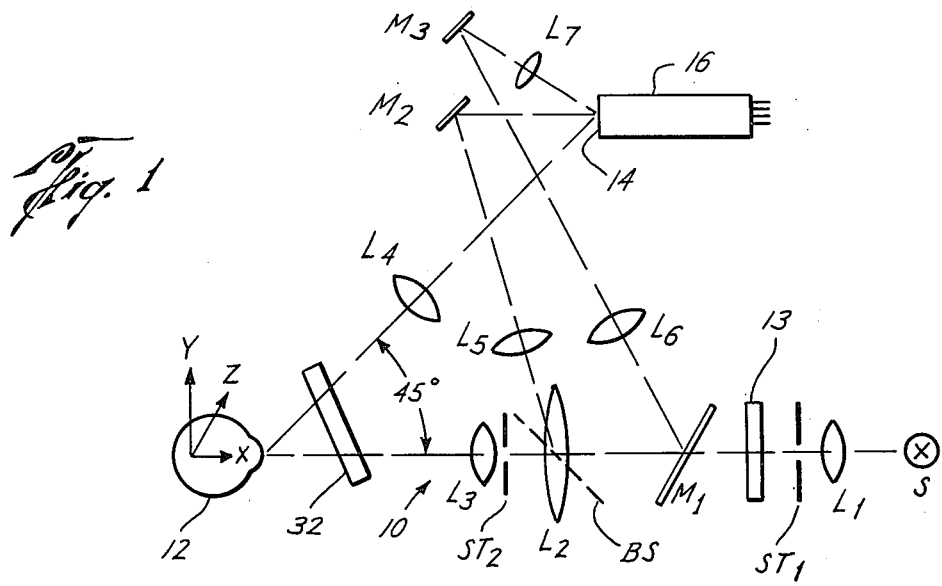
FIG. 1 is a schematic top elevational view of the optical system of the optical apparatus of the present invention.

Referring now to the drawings, and particularly to FIG. 1, the reference numeral 10 generally indicates the optical apparatus of the present invention for obtaining one or more measurements of portions of an eye 12 of a patient who is seated with his head held steady by chin and forehead supports (not shown) and directed to look at the middle of a rectangle of light hereinafter provided. The apparatus 10 generally includes means for providing a narrow beam of light through the eye in the X (horizontal) direction which may include a light source S having a vertical tungsten filament whose rays are collimated by a condensing lens $L_1$. The rays then pass through a thin vertical slit $ST_1$ which is imaged by lens $L_3$ onto the outer surface of the eye 12. Slit $ST_2$ serves to increase the depth of focus of the narrow beam of light in the X direction so that the illuminating light beam forms a sheet of light, here shown as vertical, as it passes through the cornea of the eye 12. Preferably, the light passes through a blue filter 13 which transmits only light in the deep blue region of the spectrum. This light does not appear bright to the eye, but is maximally scattered by the media of the eye and the camera 16 is maximally sensitive to the blue light. $L_2$, BS and $M_1$ do not form a part of this first lens system and will be more fully described hereinafter.

The corneal tissues scatter light in all directions, and some of that light enters a second lens means such as lens $L_4$ which forms an image of the eye 12 on the face 14 of television camera tube 16. The image formed by the lens $L_4$ is generally indicated by the reference numeral 18 in FIG. 2 on the photosensitive surface or face of a low light television camera tube, preferably an SIT camera.

It is noted that the axis of lens $L_4$ is positioned at an angle to the narrow beam of light, here indicated as 45 degrees. It is also to be noted that the face 14 of the television camera 16 is inclined to the optical axis of the lens $L_4$ at an angle, preferably but not necessarily equal to the angle between the axis of lens $L_4$ and the narrow beam of light, such as 45 degrees. The fact that the face 14 of the television camera is inclined at the same angle has the effect of magnifying the image 18 in the Z (perpendicular to both the horizontal and vertical directions) direction relative to the Y (vertical) direction (anamorphic magnification), so that the image appears just as it would if the eye were being viewed form 90 degrees or along the Z axis. This improves the sensitivity of the system for measures of curvature and thickness. Futhermore, the angle of the television camera face 14 also increases the depth of focus of the image of the eye so that deeper structures are in better focus.

Figure 2:
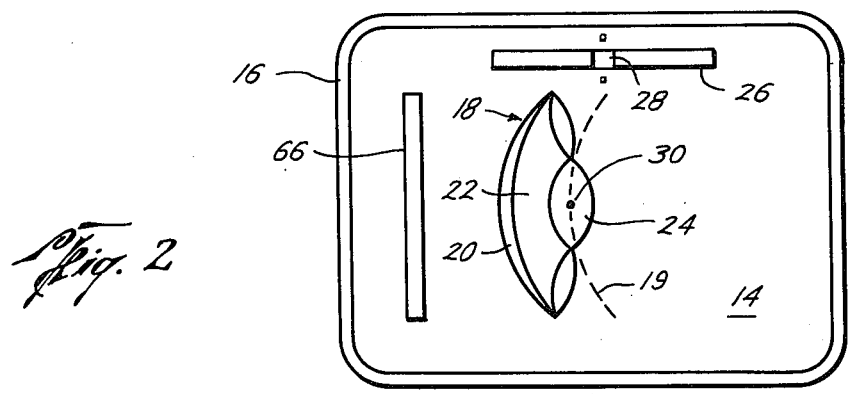
FIG. 2 is a view of the face of the tube of the television camera illustrating the images projected thereon and also a view of the television monitor.

The resulting television image 18 contains the desired information for making various measurements of the thickness of the cornea 20, the depth of the anterior chamber 22 and the thickness of the lens 24 as well as transparency measurements, but the interpretation requires accurate knowledge of the relationship between the position of the optical apparatus 10 and the eye 12. If, for example, two successive pictures were obtained, and the eye shifted sideways along the Z axis between the two pictures, they would show different curvatures, even though they were photographs of the same eye. The alignment in the vertical direction Y is not important, so long as eye 12 is in approximately the correct position so that the narrow beam of light falls on the region of the eye to be measured in the Y direction. However, alignment in the visual axis direction X is necessary in order to insure first that the narrow light beam is well focused in the eye by the lens $L_3$, secondly that the eye 12 is positioned at the correct distance from lens $L_4$ so that the image is sharply focused on the camera face 14, and thirdly, because the camera 14 is viewing the eye at an angle, motion along the X axis will produce a sideways motion of the image across the face 14 of the camera tube 16, so that improper positioning in the X direction can move the image off of the television camera.

as indicated, alignment of the apparatus 10 and eye 12 occurs in the Z direction when the narrow beam of light passes through the center of curvature of the cornea 20. One way of measuring this alignment and insuring that the beam passes through the center of curvature of the cornea 20 is to sense the light specularly reflected from the cornea by an optical system that forms an indication of the position alignment error directly on the face 14 of the television camera tube 16. This permits the operator to align the system manually by observing the television monitor or alternatively, the error signal can be electronically derived from the video output to drive a servo motor for alignment. Referring now to FIG. 1, the optical system comprising lens $L_2$, mirrors $M_1$ and $M_3$ and lens $L_6$ and $L_7$ lie above the previously described system for providing the narrow beam of light through the X, Y axis of the eye. Some of the light specularly reflected from the cornea returns in the direction of the input optical axis X, but above it, where is passes through lens $L_2$, reflects from mirrors $M_1$ and $M_3$ and through the lenses $L_6$ and $L_7$. As the eye moves sideways or laterally in the direction Z, the beam of reflected light moves across lenses $L_2$ and $L_6$, and lens $L_7$ images lens $L_6$ onto an area 28 (FIG. 2) on the face 14. A mask with a rectangular aperture covers a portion of $L_6$ resulting in a rectangular image 26 on the television face 14 as shown in FIG. 2. If the bright area 28 is centered in the rectangle 26, this indicates that the reflected beam is centered and that the apparatus 10 is aligned with the eye 12 in the Z direction. If the bright area 28 is not centered, the instrument 10 or eye 12 is moved until the bright area 28 is centered to horizontally align the instrument 10 with the eye 12.

This horizontal or Z alignment (and the vertical or Y alignment as well) can also be performed in a much simpler but less accurate way. In the sketch of the television face 14, shown in FIG. 2, a highlight 30 is shown on the face 14. If all of the optics were as described above and perfect, except that $L_2$, $L_6$, $L_7$, M, and $M_3$ were omitted, and if the Z alignment were correct so that the incident light passed through the center of curvature of the cornea, this highlight 30 would not be present. It is actually a virtual image of the light source S formed by specualr reflection from the cornea and if everything were perfect, all of the specularly reflected light would pass back along the input axis and none would enter lens $L_4$ and fall on the television camera 16. However, if the optics are not perfect, or if the stop $ST_1$ is not perfectly opaque where it is presumed to be, some light will illuminate the cornea over an area larger than the image of the slit and some of the light may enter lend $L_4$. If this occurs, this light forms the highlight 30 indicated in FIG. 2.

The exact position of the highlight 30 with respect to the leading edge of the cornea 20 depends upon the corneal curvature and on the Z position of the cornea. Therefore, if the corneal radius of curvature were known, the instrument could be aligned in the Z direction by adjusting it until the highlight 30 were some particular distance behind the leading edge of the cornea 20. It happens that the radii of curvature of human corneas vary over a limited range, such that, if the distance is determined for the average corneal radius and the horizontal alignment is performed on that basis, eyes whose radii are at the extremes of the range will still only be off-center by less than 0.2 mm, and, so long as the eye's radius does not change from one measurement to another, repeated measurements will always be on exactly the same part of the cornea even if they are not precisely on the center of curvature. Therefore, alignment in the desired direction can be achieved by generating a line 19 on the television monitor that is always precisely "d" distance to the right of the leading edge of the cornea 20, where "d" is the distance calculated for the average eye, between the leading edge and the highlight 30 when the narrow beam of light along axis X passes through the center of curvature of the cornea 20. This can be done simply by starting a one shot multivibrator when the leading edge is detected and putting a pulse into the video when the one show goes off. Then the operator changes the horizontal position control along the Z axis until the highlight 30 is centered on this generated line. Alternately, the highlight may be sensed by a circuit and the Z position automatically achieved by servo drive.

Because of the optics of convex spherical reflectors, the vertical position of the highlight 30 will always be on the same horizontal line as the vertex of the cornea 20. Therefore, it can be used for a vertical or Y direction alignment as well, simply by adjusting the apparatus 10 until the highlight 30 falls on the desired horizontal line of the television screen 14.

Any focus error in the X direction can be corrected by moving the apparatus 10 in the axial direction X. Because the image moves laterally across the television screen with changes in X position, focus errors can be sensed by sensing any horizontal departure of the image from its well-focused position and a servo motor can be driven accordingly, the servo motor in turn driving the apparatus 10 axially until focus is achieved as will be more fully described hereinafter.

As described above, the apparatus 10 obtains data about one vertical section through the eye 12. To obtain sections at other meridians, that is, such as at 45 degrees from vertical, or horizontal, the entire instrument 10 may be rotated about the optical axis X to any desired angle $\theta$ for obtaining measurements through the eye at other meridians. Alternatively, an optical system such as a system 32 of mirrors equivalent to a dove prism may be inserted between the instrument 10 and the eye 12 which, when rotated, produces the equivalent of rotating the entire optical system.

While the image 18 can be photographed or measured directly for obtaining the desired measurements, it is preferable to make the measurements electronically. The electrical signals carrying the television image 18 produced on the face 14 are fed to various signal processing circuits that are designed to extract the desired information as to thickness, curvature and transparency of various portions of the eye.

Figure 3:
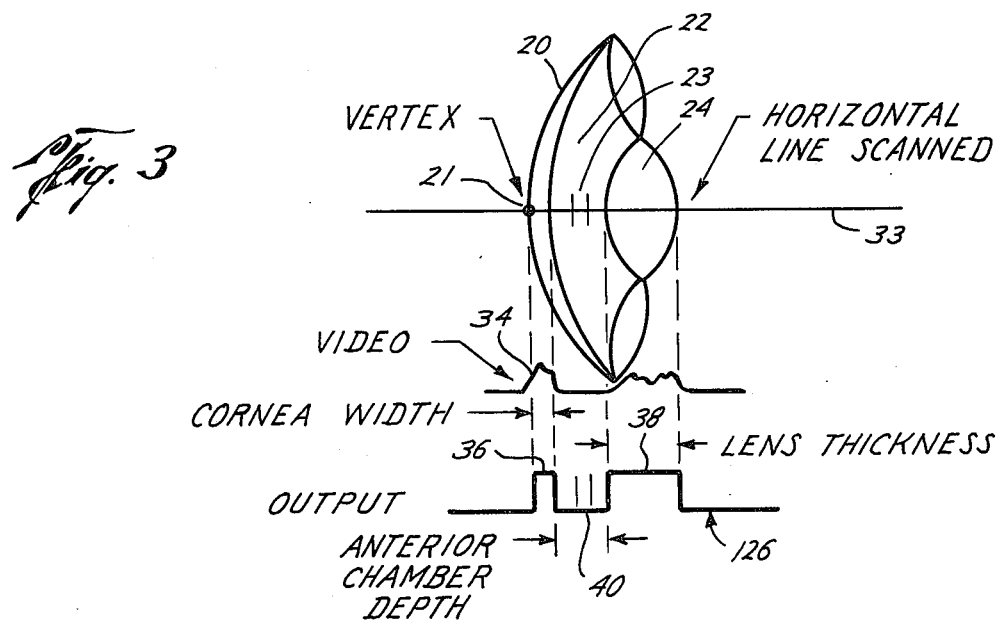
FIG. 3 is a view of the image of the eye as projected on the tube of the television camera and the relationship of a horizontal scanning line through the center of the eye with its corresponding video and processed video signal output.

FIG. 3 shows an idealized version of the television image 18 of FIG. 2. As the television camera scans across each horizontal line of the image, for example along line 33 through the center of the image 18, the voltage output, that is the video signal 34, will appear as indicated at the bottom of the image. The video signal 34 indicates a higher reflection from the cornea 20 and the lens 24 than from the anterior chamber 22. The video signal 34 is processed to form a processed video signal 126. The width of the square wave 36 of the processed signal 126 is proportional to the thickness of the cornea 20 along the horizontal line 33 scan. Similarly, the square wave 38 is proportional to the thickness of the lens 24 along the horizontal line 33 scan. And, of course, the depth of the anterior chamber 22 is the distance 40 between the square waves 36 and 38. (It is noted that at the angle of 45 degrees between the first lens system and the second lens system, used in this embodiment, the rear surface of the eye lens 24 is only visible when the pupil of the eye is dilated. Otherwise, it is hidden by the iris.)

The schematic block diagram shown in FIG. 4 illustrates the theory of measurement of thickness, here shown, for example only, as measuring the thickness of the cornea 20 of FIG. 3. In FIG. 4, the video signals from the television camera 16 transmit the image 18 on the face 14 (FIG. 2) through a high pass filter 42 to eliminate slow changes in the video level. The output of the filter 42 drives a set of threshold circuits 44 which output an impulse on line 46 at the leading edge of the cornea 20, when the video signal first exceeds a predetermined threshold, and a second impulse on another line 48 at the trailing edge of the cornea 20. The impulses on lines 46 and 48 are summed together through a summing amplifier 50 and fed to a conventional video storage device 52 which, when triggered, will retain one video picture. The distance between the leading and trailing edge pulses on any given horizontal video sweep is proportional to the corneal thickness. The leading and trailing edges are shown on the face of a conventional television monitor 54 in FIG. 5. To extract directly the data as to corneal thickness, the two impulses on lines 46 and 48, in addition to driving the storage device 52, are also fed into a digital difference amplifier 56. The difference amplifier 56 operates as follows: Each horizontal video scan begins at the left side of the picture and arrives at some vertical line, indicated by the dash line 58 on the television monitor 54, after some fixed delay. Each time the horizontal scan arrives at the dash line 58, the difference amplifier 56 is armed and fires an impulse at some time after its arming, that time being proportional to the time between the leading and trailing edge pulses entering on lines 46 and 48. The pulse output from the difference amplifier 56 is added to the other video signals on the monitor 54 producing a line at the right of the screen that is a direct plot of the distance between the leading and trailing edges of the cornea 20, that is, a plot of corneal thickness with reference to dash line 58. Hard copy of the plot on television monitor 54 may be obtained by any number of standard procedures, such as photography.

Referring now to FIGS. 6 and 7, the theory of operation of measuring the curvature of the leading edge of the cornea 20 is best seen. In FIG. 6, the video signals from the television camera 16 are processed through the high pass filter 42 and into a threshold circuit 60 which produces an impulse on line 62 but at the leading edge of the cornea 20 only. As each horizontal line is scanned, a time interval is generated that begins with the pulse that starts the horizontal sweep (the horizontal synch pulse) and ends with the pulse indicating the leading edge of the cornea. There will be a separate interval for each horizontal sweep that intersects the corneal image, each of these sweeps corresponding to a different height on the cornea. Thus, each horizontal television line generates one point in the X, Y space, a point indicating the location of the corneal surface in that X, Y space.

Although the cornea is typically not perfectly spherical, contact lenses are, and in fitting them, the cornea is usually assumed to be spherical. In fitting contact lenses, it is desirable to know the curvature of the front surface of the patient's cornea. Generally, present methods measure cornea curvature and conveniently and typically measure only the central two or three millimeters of the corneal surface, while contact lenses must fit over an appreciably larger area of the cornea. The present apparatus provides a quick, accurate and convenient means for obtaining measures of cornea curvature over any or all of the cornea. The point generated on each horizontal line establishes one point on the circle, corresponding to one meridian of the sphere, assuming that the cornea is spherical. There are only three unknowns in the equation for determining the circle. Therefore, in principle, the leading edge data on line 62 are fed into a processor 64 which can choose any three data points (that is, the outputs of any three horizontal television lines), solve three simultaneous equations, and output the radius of curvature. Preferably, the processor 64 will actually solve the equations repeatedly for various triads of data points. The resulting radii of curvature can be averaged in order to output a single number which is the average radius of curvature, which can be displayed directly on the television monitor 66 along with the profile of the leading edge, as best seen in FIG. 7.

However, the typical human cornea is not a true shere. Rather, the radius of curvature typically changes with distance from the center, such that a section through any given meridian will not be the arc of a true circle, but rather will be closer to ellipsoidal. If a contact lens is to fit well, this actual shape must be known. One way that the present instrument can output the necessary information about corneal shape is to calculate the radius of curvature at many different positions along the cornea and display a plot of radius of curvature versus position.

The fit between a given cornea and proposed contact lens can also be displayed and investigated in the following way. The corneal profile is displayed on the television monitor (with any convenient magnification) adjacent to a profile of the proposed contact lens. The operator can then move the lens profile until it just touches the corneal profile and determine the nature of the contact areas and the spaces between the lens and cornea, in order to choose a lens curvature and diameter that optimally fit the particular cornea.

In order to fit contact lenses, additional measurements are desirable because the radii of curvature of most corneas are not the same in all meridians. For example, it is commonly the case that the radius of curvature of a vertical section through the cornea will be smaller than the radius of curvature of a horizontal section through the same cornea. The corneal surface is then a toric surface, and the patient will be said to have astigmatism. Generally, in order to measure the desired values, the entire operation that was described above is repeated at each of four meridian angles. For example, the curvature is measured with the narrow beam vertical, then again with the apparatus 10 rotated about the X axis to an angle $\theta$ so that the narrow beam lies at $\theta=45°$ to the vertical, then at $\theta=90°$, that is horizontal, and once more at $\theta=135°$. The resulting four measures of cornea curvature are then fed into the processor 64 which now solves the equation relating radius of curvature to meridian angle for a simple toric surface and outputs the computed values for the three unknowns. These values can be used directly in the fitting of contact lenses and in the evaluation of the nature of a person's astigmatism.

As indicated, the present apparatus 10 by suitably processing the video signals can measure thickness and curvature of various parts of the eye. In addition, the present apparatus may also be used to measure transparency of various portions of the eye. For example, when the transparency of the cornea is reduced, the reduction in transmission is almost always the result of an increase in the scattering of light by the corneal tissue, rather than an increase in absorption. Therefore, a measurement of the intensity of the scattered light is also a measure of the transparency of the cornea, and is a parameter that is of great interest to ophthalmologists when they deal with corneal pathology. However, if the intensity of the light is to be measured, the measurement should be independent of the aging of the light source S or changes in the lamp voltage, or changes in the sensitivity of the camera.

Figure 8:
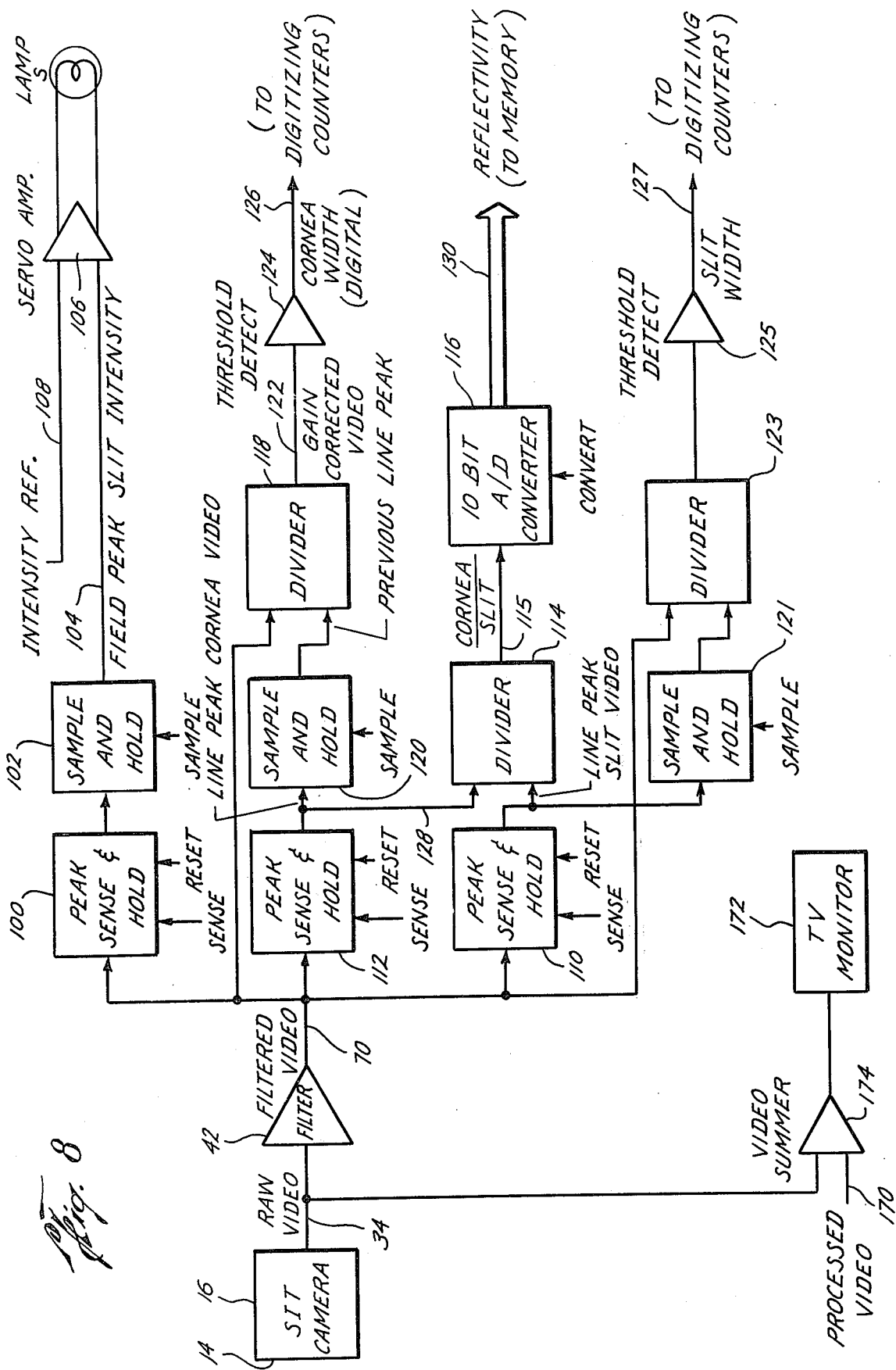
FIG. 8 is a block diagram of the video analog processor of the preferred embodiment of the present invention.

Referring again to FIG. 1, BS is a beam splitter which reflects a small portion of the light from the light source S through lens $L_5$ which forms an image of the slit $ST_1$ on the face 14 of the camera tube 16, after reflection from mirror $M_2$. This image 66 (FIG. 2) is the same length as the image of the slit as diffusely reflected from the eye and is projected on the left side of the television face 14. The image 66 is used to control the brightness of the lamp source S and to correct for local inhomogeneities in the intensity of the illumination on slit $ST_1$. That is, as best seen in FIG. 8, the filtered video signal on line 70 passes through a circuit 100, which will be more fully described hereinafter, which determines the video level corresponding the the brightest part of the slit image 66 which provides one input 104 to a servo amplifier 106, the other input 108 being a reference input to control the current through the lamp source S in order to maintain the video output of the image 66 at a constant level, independent of changes inherent in the lamp source S or fluctuations in the gain of the television camera 16. While this intensity control system is not strictly necessary, for reasons given hereinafter, it makes the operation of the instrument 10 somewhat easier. For example, the operator initially sets the intensity of the lamp source S by varying the intensity reference 108, at a level where the video signal from the eye 12, as output from the camera 14, is below saturation and in its linear range. The automatic control relieves the operator of having to watch for occurrences such as drifts in lamp brightness or camera gain which could cause the signal to enter its nonlinear range.

As previously indicated, transparency measurements, such as the transparency of the cornea 20, the anterior chamber 22 or the lens 24 can be indicated by measuring the amplitude of the video signals corresponding to the images of the cornea 20, anterior chamber 22 and lens 24 (FIG. 3), respectively. Preferably, as will be more fully described hereinafter, as each horizontal television line is swept, the image 66 of the slit is scanned first. The peak video during each scan of the slit image 66 is sent and stored in a circuit 110 (FIG. 8). Next, on the same horizontal video sweep, the peak of the video for the portion of the eye to be meausred, such as the cornea 20, is sent and stored in a circuit 112. Then the ratio of the amplitude of the cornea measurement to the amplitude of the slit image 66 is computed in a divider 114 and stored in a memory through an A/D converter 116 for each horizontal television line swept. This ratio is a measure of the diffuse reflectivity of the cornea that is unaffected by variations in the intensity of the illumination of the slit $ST_1$. This comparison, along each horizontal television line, of the brightness of the slit $ST_1$ with the brightness of the cornea image 20 illuminated by that part of the slit $ST_1$ corrects for any local inhomogeneities in the brightness of the slit $ST_1$.

The above described method of measuring the transparency of the cornea 20 can also be similarly applied to measure the transparency, or really the diffuse reflectance, of the aqueous humor (FIG. 3), the fluid that fills the anterior chamber 22. This measurement can be made in the same way as the measurement of corneal transparency, except that the peak detector circuit is gated to measure the average video amplitude of the video signal in an area 23 between the trailing edge of the cornea 20 and the leading edge of the lens 24 (FIG. 3) along the horizontal line 33 containing the vertex of the cornea 21. This measurement is of interest in treating certain diseases of the eye that cause the aqueous humor to turn milky.

In measuring leading edges, trailing edges, and consequently thickness of portions of the eye such as the cornea 20, the anterior chamber 22 and the lens 24, it is important that accurate measurements be made of the edges on each horizontal television line. These measurements are subject to errors if the image is out of focus and/or if the image changes in intensity. For example, if the system is set to define the leading and trailing edges as the points when the video signal just emerges from the background noise, errors of focus will spread the light and thus give erroneously large thickness readings. If the edges are defined as points where the video signal is substantially larger than the background level, differences in intensity from one part of the image to another would appear as differences in width. To avoid errors in measuring edges caused by focus and intensity changes, the edge can be defined as the point at which the video signal reaches half of its maximum. Assuming that the change in intensity of the measured image from one horizontal line to the next horizontal line is negligible, this can be achieved, say for the cornea, by comparing the peak video in the image of the cornea during each television line with a reference voltage, for example, one volt, and changing the gain on the next line in proportion to the difference between the measured video and the reference. This will produce a constant video level (for example approximately one volt) during each line's horizontal scan, assuming small level changes between consecutive horizontal lines. If the edges are then defined as those parts where the video signal is 0.5 volts, the edges and the thickness measurements will be unaffected by changes in focus or brightness.

Another measurement that may be made is the depth of the anterior chamber 22, as best seen in FIG. 3. The anterior chamber is the space between the rear surface of the cornea 20 and the front surface of the lens 24, and its depth is simply the distance from the rear of the cornea 20 to the front of the lens 24. Therefore, a measure of the distance between the rear of the cornea 20 and the front of the lens 24, along the horizontal television line that passes through the corneal vertex, which is determined as will be more fully described hereinafter, will be the depth of the anterior chamber 22. This measurement is performed in the same way as the measurement of the corneal thickness 20 and is of interest in evaluating a patient's susceptibility to closed angle glaucoma. Similarly, a measurement of the thickness of the lens 24 can be made along a line approximately through the center of curvature of the lens by measuring the difference in the leading and trailing edges of the lens 24 on the horizontal line containing the control vertex. These distances, such as from the front to the back surface of the lens, are distorted in well known ways by the optics of the eye before they are imaged on the camera tube. Therefore, for very accurate measurements, corrections should be applied to compensate for the distortions.

Referring now to FIG. 8, a block diagram of the video analog processor is best seen which is connected to the camera 16 for processing the video signals received by the camera 16 on its face 14 of the image 66 of the slit and of the image 18 from the eye. The video signals pass from line 34 through the filter 42 and are transmitted to three peak sense and hold circuits 100, 110, and 112. Each horizontal video line scanned by the camera 16 is separated for processing the slit image 66 and the eye image 18. As previously indicated, during the window for measuring the slit image 66, the peak video for the slit image 66 is sensed and held in circuit 100 and is stored for each horizontal line accumulative for a complete video field. The remaining level in circuit 100 at the end of a complete video field is the peak intensity of the slit image 66. This level in circuit 100 is sampled by sample and hold circuit 102 at the end at each video field and transmitted to one input 104 of a servo amplifier 106, whose other input 108 is connected to an intensity reference. Servo 106 controls the intensity of lamp S equating the peak field intensity 104 from circuit 102 to the intensity reference 108 thus compensating for variations in camera gain and lamp properties. The peak sense and hold circuit 112, gated by the cornea window, detects the peak video levels for the cornea for each horizontal line. Similarly, the peak sense and hold circuit 110, gated by the slit window, detects the peak video level for the slit for each horizontal line. The output of peak sense and hold circuit 112 is sampled and held in sample and hold circuit 120 at the end of each horizontal line and divided by divider 118 into the video level 70 for the next line to provide a normalized or gain controlled video level on line 122 which is detected by a threshold detector 124 to generate a pulse on output 126 which is indicative of the width of the cornea for each line.

To minimize measurement errors due to short term sweep variations, and to compensate for inhomogeneities in the camera tube, the reference for measurements of cornea leading edge (curvature) is the slit trailing edge. To detect the slit trailing edge, the slit video must be normalized and threshold detected. This is accomplished, as the cornea width is determined, by sample and hold 121, divider 123, and threshold detector 125 to generate an output slit width 127.

In addition, the peak cornea level from circuit 112 is transmitted along line 128 to a divider 114 where the peak cornea level is divided by the peak slit level from circuit 110 for each horizontal line to generate a normalized analog equivalent of diffuse reflectivity or transparency of the cornea which is degitized by A/D converter 116 to a binary equivalent of diffuse reflectivity for each horizontal line and outputted on lines 130 to a memory.

Referring now to FIG. 9 of the drawings, a block diagram of the logic is shown. A set of switches 132 is provided to select the mode of operation such as "monitor", "store", and "record" which controls the actuation of a controller 134. A timing signal is supplied at line 136, such as a 50.4 MHZ timing signal to the controller 134. A first 138 and a second 140 high speed counter are provided connected to the controller as indicated. The pulses indicative of the corneal width on output 126 and slit width on 127 (FIG. 8) are also supplied to the controller 134 and in turn to the high speed counters 138 and 140 to properly enable counters 138 and 140 which count to generate a binary equivalent of cornea leading edge and thickness. A clock input 142 is supplied to the first counter 138 to supply data relative to the leading edge of the cornea, and a clock input 144 is supplied to the second counter 140 providing information as to the distance from the leading edge of the cornea to the trailing edge of the cornea.

During field one of a video frame, if the controller 134 is in the monitor mode selected by depressing the monitor switch, the input information on lines 126, 127, 142 and 144 is presented to the counters 138 and 140 to generate a binary equivalent of: (a) distance from trailing edge of slit to the leading edge of the cornea, (b) distance from the leading edge of the cornea to the trailing edge of the cornea. This information is outputted from lines 146 and 148, along with the binary equivalent of reflectivity on line 130 (FIG. 8) to a memory 150 for each line of field one.

The output 146 from the counter 138, which is the magnitude of the distance from the slit trailing edge to the leading edge of the cornea is also transmitted to a magnitude comparator and memory 152 where this binary number is compared to the binary number 146 of the preceding line for every line of field one and the smaller binary number is retained for comparison to the next line. The remaining number of the end of field one is the vertex 21 (FIG. 3) of the cornea, that is, the point on the leading edge of the cornea closest to the beginning of the horizontal sweep line. This number is compared to a number representing line 19 (FIG. 2) which corresponds to proper focus, with the difference being the focus error signal 154 (a binary number).

As best seen in FIG. 11, the focus error 154 is applied to a digital to analog converter 156 generating an analog equivalent of focus error which is applied to a position servo amplifier 160 and in turn operating a focus motor 162 which is connected to the apparatus 10 for moving the apparatus in the X direction to correct the focus. A manual focus control 164 is provided for manually actuating the focus motor 162.

During field two of a frame with the controller 134 in the monitor mode, the information stored in the memory 150 for both the leading edge and thickness of the cornea is presented sequentially by line and loaded through lines 166 and 168 in parallel into the high speed counters 138 and 140, respectively. During the time interval of a line, the high speed timing signal decrements the counters 138 and 140. At zero count, terminals CO (count zero) is sensed and a pulse is generated through line 170 to the television monitor 172 (FIG. 8) as cornea leading and trailing edge.

If the "store" switch of the mode selection switches 132 is depressed and when the cornea is in focus, the last field one information is retained in memory 150 and the controller 134 enters the "store" mode. During "store" mode, the video summer 174 gates off the raw video and only the processed video is transmitted to the television monitor 172.

In subtractor 176, for each line the binary equivalent of the vertex is subtracted from the leading edge binary equivalent to provide an output binary number, the stored corrected leading edge 178, which together with the stored thickness 168 are presented to the high speed counters 138 and 140, respectively, and parallel loaded sequentially during "store" mode field one. The counters 138 and 140 are then decremented for each line by a lower speed timing signal to generate pulses as a processed video image on line 170 to the television monitor 172 to provide a video picture on the monitor 172 which are lines indicative of the cornea leading and trailing edge magnified by the ratio of the 50.4 MHZ timing signal to the lower speed timing signal with the vertex shifted to the left-most portion of the television monitor screen.

Similarly, during field two of "store" mode, the binary equivalents of thickness and reflectivity are transmitted from the memory 150 to the counters 138 and 140 to generate lines indicative of these measurements on the television monitor 172. The television picture on the monitor 172 will be a time multiplex composite of field one and field two appearing as a single display to the eye.

If the information on the television monitor is satisfactory, the "record" switch of the mode select switches 132 may be depressed to enter the "record" mode and the information is transmitted from memory 150 through selectors 175 and 177 to a digital analog converter 174 to an output line 176 to a recorder such as a chart recorder to make permanent records of (1) the cornea leading edge, and (2) the cornea leading edge plus the thickness (cornea trailing edge). A third recording is made of the numbers representing thickness which are presented through the D/A converter 174 to a recorder. And a fourth recording is made of numbers representing the reflectivity or the transparency of the cornea.

As described above, the leading and trailing edges, the thickness and the transparency of the cornea were measured. As described in connection with FIG. 3, the measurements of additional portions of the eye may be made such as the depth and transparency of the anterior chamber 22 and the thickness of the lens 24.

During field one in "monitor" mode, measurements were to determine the horizontal video line containing the vertex 21 of the cornea 20. During field two, measurements are made of the anterior chamber, which is the area between the trailing edge of the cornea 20 and the leading edge of the lens 24. Referring now to FIG.

10, a controller 180 is provided which has input 182, 184, 186, and 188, which are, respectively, indication of the horizontal line containing the vertex, cornea width output 126 (FIG. 3), a high speed clock timing signal, and a mode control signal. During "monitor" mode, field two, a high speed counter 188 is enabled by controller 180 and counts during the interval 40 (FIG. 3) by output 126 on the horizontal line determined to contain the vertex. The binary number represents the depth of the anterior chamber and is transmitted to a memory 190 and through a selector 192 to an ROM 194 which converts the binary number to BCD number representing the depth of the anterior chamber 22 in millimeters to a panel display 196. Similarly, a high speed counter 199 is enabled and counts during the interval 38 (FIG. 3) on the longitudinal line containing the vertex and the binary number represents the thickness of lens 24 and is transmitted to a memory 191 and through selector 192 to ROM 194 to display 196.

When the horizontal line containing the vertex is sensed during "monitor" mode, field two, a high speed analog to digital converter 198 is enabled whose input is cornea/slit video 115 (FIG. 8). Samples along the video line are digitized and the resulting binary numbers represent the normalized video level at the sampled points. A representative number (for example eight) of points in an area near the center of the anterior chamber 22 are summed in an adder 200, divided by the number of samples (here taken as eight) and stored in memory 201. This binary number represents a proportionality to the transparency of the anterior chamber. This binary number is retained during "store" and "record" modes, presented to the ROM 194 through selector 192 and displayed on panel display 196.

In addition, when the horizontal line containing the vertex is sensed, the output of the high speed A/D converter 198 for the samples between the leading and trailing edge of the lens 24 are stored in a memory 202 whose output is D/A converted by D/A converter 204 at a much lower speed during "record" mode and presented to an output 206 for presenting to a suitable recorder, such as a chart recorder. This recording is a profile of the transparency of the lens 24. Samples from the A/D converter 198 during an interval 23 (FIG. 3) are presented to adder 200, averaged, and presented to memory 201, selector 192, ROM 194, and display 196 as average anterior chamber transparency.

Referring to FIG. 11, a schematic of the positioning servos is shown. The entire apparatus 10 can be positioned in all three directions (X, Y and Z) as well as rotated about its axis X to any desired angle $\theta$. The $\theta$ positioning control 208 is manual and its angle of rotation determines the meridian of the eye to be viewed and recorded by actuating a servo amplifier 210 which drives a motor 212 for rotating the apparatus 10 about the X axis to an angle $\theta$. Control of the apparatus in the direction X may be manually controlled in the initial set-up by manual focus control 164. Irrespective of the angle of rotation $\theta$, the view of the eye will be seen on the television monitor 172 as shown in FIG. 3. For positioning, vertical movement is along the tangent to the cornea at the vertex as seen on the television monitor and horizontal movement is perpendicular to this tangent. To accomplish movements in these directions, Y and Z simultaneous drives must be generated as a function of the angle of rotation $\theta$. A sine/cosine converter 222 is attached to the $\theta$ position sensor such that the sine and cosine of the angle $\theta$ are generated. These signals in addition to signals representing Y and Z position are applied to horizontal and vertical drive generator 215 where Y drive and Z drive are generated and applied to Y servo 220 and Z servo 218 such that the speeds of Y motor 221 and Z motor 219 are controlled to move the image on monitor 172 in either the horizontal or vertical direction as selected by horizontal and vertical controls 214.

The present invention, therefore, is well adapted to carry out the objects and attain the ends and advantages mentioned as well as others inherent therein. While a presently preferred embodiment has been given for the purpose of disclosure, numerous changes may be made without departing from the spirit and scope of the invention as hereinafter claimed.

What is claimed is:
1. An optical apparatus for obtaining one or more measurements of portions of an eye comprising,
   means for providing a narrow beam of light through the center of curvature of the cornea of the eye including a light source, first lens means, and at least one narrow slit,
   second lens means positioned in front of the eye but at an angle to the narrow beam of light for collecting light that is reflected from the eye,
   a television camera positioned to receive the eye image collected by the second lens means, said television camera co-acting with means for obtaining the desired measurements of portions of the eye
   means for measuring when the narrow beam of light passes through the center of curvature of the cornea for indicating alignment of the eye with said television camera, and
   means for focusing light on the eye and for focusing the reflected eye image on the television camera for measuring when the eye is correctly positioned along the optical axis of the apparatus for proper focus in the first and second lens means.
2. The apparatus of claim 1 wherein the face of the television camera is positioned to receive the image collected by the second lens means at an angle other than 90 degrees to the optical axis of the second lens means.
3. The apparatus of claim 1 including,
   means connected to the television camera for receiving the video signals from said camera and measuring the positions of the leading and trailing edges of a portion of the eye and determining the difference between the leading and trailing edges which is a measurement of thickness of said eye portion, and
   storage means connected to the means connected to the television camera for storing said data relative to the thickness.
4. The apparatus of claim 1 including, means connected to the television camera for receiving the video signals and measuring the leading edge of the cornea, and
   a processor receiving the measured data relative to the leading edge of the cornea and determining the curvature of the leading edge of the cornea.
5. The apparatus of claim 1 including,
   means for maintaining the light output of the light source multiplied by the gain of the camera constant.
6. The apparatus of claim 5 wherein the light measuring means includes, means for reflecting a portion of the narrow beam of light onto the television camera, means connected to the video signal of the camera for measuring the intensity of the video signal corresponding to the vertical beam of light on the camera, and a servo amplifier having one input connected to the means measuring the intensity of the video signal corresponding to the vertical beam on the camera, and a second input connected to a light intensity reference, and the output of the amplifier connected to the light source.

7. The apparatus of claim 1 including, means connected to the television camera for receiving the video signals from the camera for measuring the transparency of one portion of the eye including means for measuring the amplitude of the video signals in the television camera corresponding to the image of said one portion of the eye.

8. The apparatus of claim 7 including,
means for reflecting a portion of the narrow beam of light onto the television camera, and
means for comparing the amplitude of the video signals corresponding to the image of said one portion of the eye with the amplitude of the video signals corresponding to the beam of light on the camera.

9. The apparatus of claim 3 wherein the leading and trailing edges are determined by means locating the places where the video signals are substantially midway between the minimum and maximum video signal along each horizontal sweep.

10. The apparatus of claim 1 including,
means connected to the television camera for receiving the video signals passing through the vertex of the cornea and measuring the depth of the anterior chamber of the eye by measuring the trailing edge of the cornea and the leading edge of the lens.

11. The apparatus of claim 1 including,
means for measuring the transparency of the aqueous humor of the eye including means for measuring the amplitude of the video signals in the television camera corresponding to the image of the anterior chamber of the eye.

12. The apparatus of claim 1 wherein the means for measuring when the eye is correctly positioned along the axis perpendicular to the axis of the narrow beam of light so that the narrow beam passes through the center of curvature of the cornea including,
means for generating a line on the television camera a predetermined distance from the leading edge of the cornea whereby the position relative to the center of curvature of the cornea is determined by the relative position of the line and the image of the light source on the camera formed by specular reflection from the cornea.

13. The apparatus of claim 1 wherein the means for measuring when the narrow beam passes through the center of curvature of the cornea includes,
an optical system, past of which is positioned above the plane of the narrow beam, for projecting light specularly reflected from the cornea onto the television camera, and
indicator means on the camera indicating by reference to the specularly reflected light the position of the center of curvature of the cornea relative to the apparatus.

14. The apparatus of claim 1 including,
means for rotating the apparatus about the optical axis of the first lens means for obtaining measurements along other meridians of the eye.

15. The apparatus of claim 3 wherein the measuring means measures the leading and trailing edges of the cornea.

16. The apparatus of claim 3 wherein the measuring means measures the leading and trailing edges of the lens.

17. The apparatus of claim 8 wherein the transparency of the cornea is measured wherein the comparing means compares the amplitude of the video signals corresponding to the image of the cornea with the amplitude of the video signals corresponding to the reflected beam of light.

18. The apparatus of claim 8 wherein the transparency of the lens is measured wherein the comparing means compares the amplitude of the video signals corresponding to the image of the lens with the amplitude of the video signals corresponding to the reflected beam of light.

19. The apparatus of claim 8 wherein the transparency of the anterior chamber is measured wherein the comparing means compares the amplitude of the video signals corresponding to the image of the anterior chamber with the amplitude of the video signals corresponding to the reflected beam of light.

20. The apparatus of claim 1 wherein the face of the television camera is positioned at an angle to the optical axis of the second lens means equal to the angle between the optical axis of the first and second lens means.

21. The apparatus of claim 1 including means for locating the vertex of the cornea including,
means for reflecting a portion of the narrow beam of light onto the face of the television camera,
means connected to the camera for receiving the video signals of the camera,
means for measuring the distance from the image of the narrow beam of light to the image of the leading edge of the cornea for each horizontal sweep of the video signals, and
comparatory and memory means connected to the measuring means for comparing the distances and retaining the smaller distance which locates the vertex of the cornea.

22. The apparatus of claim 21 including,
means for comparing the position of the vertex with the predetermined assumed position of the vertex and providing an output indicating focus error,
focus means connected to the apparatus for receiving said output for moving said apparatus to correct for focus error.

* * * * *

UNITED STATES PATENT OFFICE
CERTIFICATE OF CORRECTION

Patent No. 4,019,813    Dated April 26, 1977

Inventor(s) Tom N. Cornsweet et al.

It is certified that error appears in the above-identified patent and that said Letters Patent are hereby corrected as shown below:

```
Column 3, line 55, change "form" to --from--
Column 4, line 19, change "as" to --As--
Column 4, line 38, change "is" to --it--
Column 4, line 63, change "specualr" to --specular--
Column 4, line 3, change "lend" to --lens--
Column 4, line 32, change "show" to --shot--
Column 7, line 44, change "shere" to --sphere--
Column 8, line 50, delete the second occurrence of "the"
Column 15, line 60, change "past" to --part--
```

Signed and Sealed this

Thirteenth Day of September 1977

[SEAL]

Attest:

RUTH C. MASON
Attesting Officer

LUTRELLE F. PARKER
Acting Commissioner of Patents and Trademarks